US007513359B2

(12) United States Patent
Bob et al.

(10) Patent No.: US 7,513,359 B2
(45) Date of Patent: Apr. 7, 2009

(54) DISCONTINUOUS LINEAR DRIVE

(75) Inventors: Konstantin Bob, Weinheim (DE); Fritz Pauker, Kissing (DE)

(73) Assignee: INVENDO Medical GmbH, Weinheim (DE)

( * ) Notice: Subject to any disclaimer, the term of this patent is extended or adjusted under 35 U.S.C. 154(b) by 9 days.

(21) Appl. No.: 11/432,709

(22) Filed: May 11, 2006

(65) Prior Publication Data
US 2006/0254884 A1 Nov. 16, 2006

(30) Foreign Application Priority Data
May 12, 2005 (DE) .................. 10 2005 022 132

(51) Int. Cl.
B65G 23/24 (2006.01)
B65G 22/24 (2006.01)
(52) U.S. Cl. .................. 198/780; 474/157; 474/902; 474/903; 74/438; 74/451
(58) Field of Classification Search .................. 198/780; 74/89.23, 438; 474/157, 902
See application file for complete search history.

(56) References Cited
U.S. PATENT DOCUMENTS
3,930,566 A * 1/1976 Matsushima .............. 192/223.4

4,076,018 A 2/1978 Heckele
6,048,307 A 4/2000 Grundl et al.
2003/0149338 A1 8/2003 Francois et al.

FOREIGN PATENT DOCUMENTS
DE    7440701       4/1975
DE    3925484       2/1991
EP    1183990       3/2002
EP    1186800 A1 *  3/2002
EP    1212975       6/2002
WO    9953827       4/1999
WO    0208035       2/2001
WO    03030727      10/2002

OTHER PUBLICATIONS

Official Action of German Patent Office for related application 102005/022132.7 dated Mar. 6, 2006, 5 pages.
Search Report and Written Opinion of European Patent Office for the related application 06110969.0 dated Aug. 10, 2006, 5 pages.

* cited by examiner

*Primary Examiner*—Gene Crawford
*Assistant Examiner*—Kavel P Singh
(74) *Attorney, Agent, or Firm*—Hanley, Flight & Zimmerman, LLC

(57) ABSTRACT

A discontinuous linear drive comprises a guiding component and an engaging means. The engaging means engages in a member to be driven and guided by guiding components in at least two places by means of a respective movable engaging component. The member to be driven is driven by a phase-shifted effecting and releasing of the engagement of the moved engaging components.

12 Claims, 2 Drawing Sheets

DISCONTINUOUS LINEAR DRIVE

BACKGROUND OF THE INVENTION

1. Field of the Invention

The invention relates to a discontinuous linear drive comprising a guiding component and an engaging means which drives forward an element guided by the guiding means.

2. Discussion of the Prior Art

From prior art, for instance according to DE-OS 39 25 484 of the applicants themselves, a discontinuous drive of this species is known. In said drive two axially spaced support members are provided in the form of radially expandable supporting rings which are coupled to each other via a sleeve-shaped spacer. The spacer is mainly formed by a piezoelectric element or hydraulically operable bellows which, accordingly, are variable in their axial length.

For a progressive movement it is provided to alternately radially expand the two supporting rings and contract them again and, in so doing, to push forward the supporting ring which is currently not supported or rather pull it along by expanding or contracting the spacer. Such a linear drive pulls a load or a component to be conveyed for instance into a tubular cavity, the axial supporting rings being supported on the inside of the cavity wall.

Although in this way a controlled progressive movement is possible, the known discontinuous linear drive requires an external support, for instance the afore-mentioned cavity wall, so that the use thereof is not always possible or, rather, can take place only after expensive conversion measures and adaptations to the spatial circumstances.

Therefore, the invention is based on the object to provide an improved and cost-effective linear drive of this species.

SUMMARY OF THE INVENTION

The object of the invention is achieved by a discontinuous linear drive comprising the features according to claim 1. Consequently, the core of the invention consists in the fact that the discontinuous linear drive, inter alia, comprises a guiding component guiding a member to be driven and an engaging means which is adapted to be engaged with the member in at least two places by means of a linearly movable engaging component (3a, 3k). Then, the guided member is driven by a phase-shifted effecting and releasing of the engagement of the movable engaging components (3a, 3k).

Accordingly, by virtue of the afore-described drive concept the guiding component is stationary and thus serves as an internal support for the forward drive. The linear drive of this design operates largely independently of local circumstances and, consequently, needs not be adapted to different marginal conditions such as, for instance, the internal dimension of a cavity to be explored. Therefore, such a standard design of a discontinuous linear drive is by far more cost-effective and functional than the drives known from prior art and, consequently, is basically suited for use as a throw-away article.

Further advantageous embodiments of the invention are the subject matter of the subclaims.

BRIEF DESCRIPTION OF THE DRAWINGS

Hereinafter the invention will be explained in detail by way of a preferred embodiment with reference to the accompanying drawings.

DETAILED DESCRIPTION OF THE PREFERRED EMBODIMENT

Figure 1:
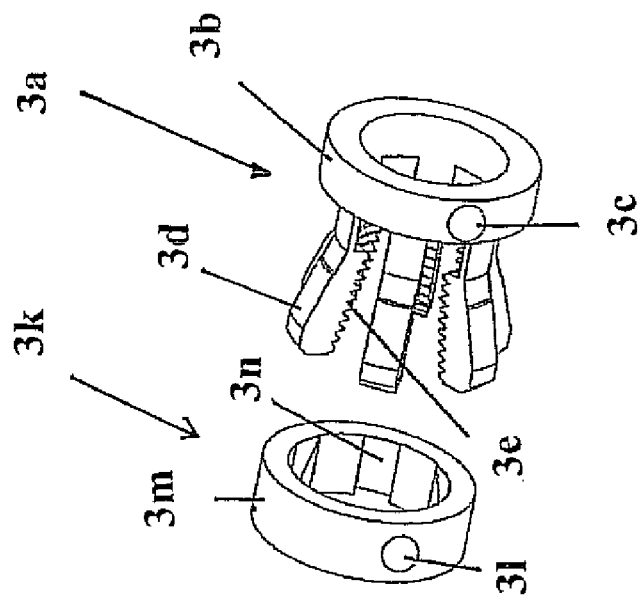
FIG. 1 shows the discontinuous linear drive of the present invention in a partially exploded view.
Figure 1:
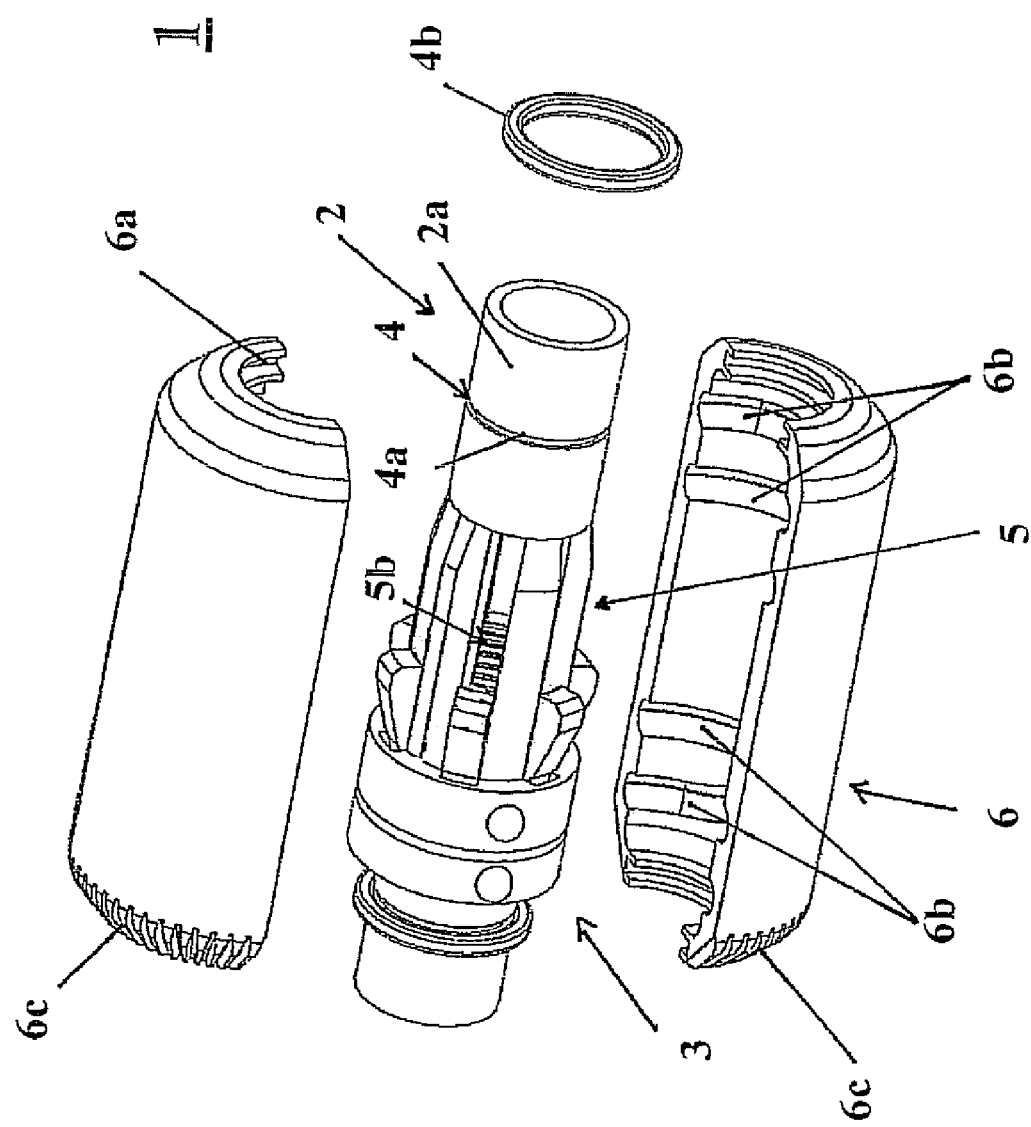
Figure 2:
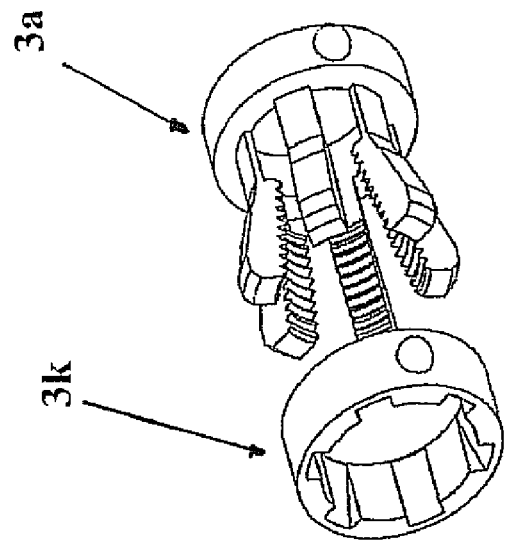
FIG. 2 shows the discontinuous linear drive of FIG. 1 from a different perspective.
Figure 2:
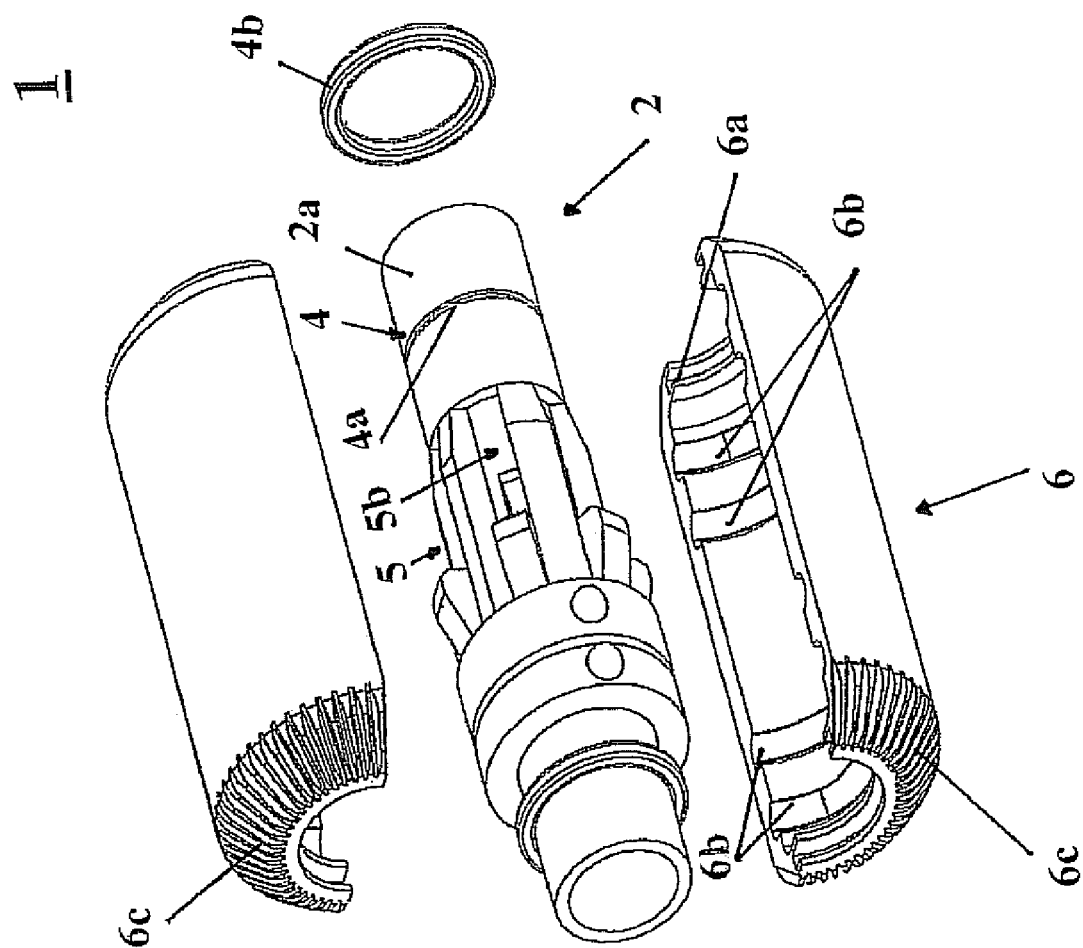

The discontinuous linear drive 1 of the present invention is represented in FIGS. 1 and 2 in an exploded view and seen from different perspectives. All components of the present linear drive are preferably manufactured by injection molding, however further materials which are inexpensive in their manufacture and for which merely a single use is profitable due to the inexpensive manufacturing costs can equally be used.

As one can take from the Figures, the discontinuous linear drive 1 basically consists of a guiding component 2 and an engaging means 3.

The guiding component 2 preferably is a tubular component 2a or a tube-or sleeve-shaped component. In the tubular component 2a (or, rather, in the cavity thereof) a member to be driven (not shown) is provided, for instance the shaft of an endoscope or an everting tube covering the same, which is to be driven by the discontinuous linear drive 1. The tubular component 2a preferably consists of three axially spaced portions arranged in series, i.e. of two axially spaced end portions and an interposed central portion. The outer diameters of the two end portions are substantially equal, whereas the central portion has a slightly larger outer diameter. The transition between the two end portions to the central portion is not abrupt but gradual with a cone being formed. The inner diameters of all three portions are substantially equal.

However, also other transition shapes than the afore-described linear or conical transition are possible. For instance, a convexly or concavely extending transition between the respective end portion and the central portion can be taken into account. It is also possible that all three said portions of the tubular component 2a have substantially equal outer diameters. The inner diameter of the tubular component 2a, however, constantly remains the same in the preferred embodiment through all afore-mentioned portions and, consequently is constant along the entire tubular component 2a.

Each of the end portions of the tubular component 2a is equipped with a bearing means 4 preferably representing a bearing which is movable in the circumferential direction of the tubular component 2a and is stationary in the axial direction thereof.

To put it more concretely, the bearing means 4 is in the form of a peripheral groove 4a disposed at the respective end portion of the tubular component 2a, as can be taken from FIG. 1 or 2. Furthermore the bearing means 4 includes a slide ring 4b inserted in the groove 4a which has such dimensions that a part thereof (an outer circumferential portion of the slide ring 4b) forms a projection peripheral at the end portion of the tubular component 2a or a shaft step, respectively. The functioning of the bearing means 4 and of the groove 4a and the slide ring 4b inserted therein, respectively, will be discussed in detail hereinafter, when the further means and components relevant hereto have been described.

The central portion of the tubular component 2a preferably is designed such that the afore-mentioned engaging means 3 can be movably mounted thereon in axial direction of the tubular component 2a, which will be discussed in detail hereinafter. In more concrete terms, the central portion of the tubular component 2a is provided to include a guide means 5 for guiding the engaging means 3. In the present embodiment it is in the form of recesses or slits 5b extending in the longitudinal direction of the tubular component 2a or the central portion over a predetermined distance, preferably over the entire length of the central portion. Preferably plural recesses 5b evenly spaced along the circumference of the tubular component 2a are provided. Since the depth of the recesses 5b corresponds to the thickness (tube thickness) of the tubular component 2a, the recesses 5b constitute through slits at the central portion of the tubular component 2a.

The through slits 5b may have any design. Preferably a rectangular shape is chosen. But a slit which is closed at the two axial ends thereof by a semi-circular edge is equally imaginable.

In the afore-described guide means 5 and in the above-mentioned through slits 5b the already mentioned engaging means 3 described hereinafter in detail is inserted.

The engaging means 3 guided by the guide means 5 and the through slits 5b, respectively, substantially consists of at least two engaging components each of which has an engaging member 3a and a clamping member 3k.

Preferably the engaging member 3a is provided at least partly in an annular shape, whereby an annular portion 3b of the engaging member 3a is formed. The inner diameter of the annular portion 3b of the engaging member 3a substantially corresponds (slight oversize) to the outer diameter of a corresponding end portion of the tubular component 2a, whereby the engaging member 3a is adapted to be slidingly slipped onto the tubular component 2a. The inner diameter thereof may equally correspond to that of the central portion. This will be discussed in detail hereinafter.

The annular portion 3b of the engaging member 3a comprises a catch, preferably a projection or cam 3c, at the outer circumference thereof which may have a hemispherical shape. Also other configurations are possible, however, such as, e.g., a radially projecting pin or a negative catch such as an external groove or flute extending in the circumferential direction of the annular portion 3b, as long as the purpose of use defined for that can be obtained, as will be described hereinafter in detail.

Moreover, the engaging member 3a further comprises a clamping portion 3d in addition to the annular portion 3b. The clamping portion 3d consists of at least one possibly wedge-shaped clamping finger or claw extending in axial direction of the annular portion 3b the root of which originates from the end face of the annular portion 3b. Preferably the clamping portion 3d forms a plurality of clamping fingers evenly spaced apart in circumferential direction of the annular portion 3b of the engaging member 3a. The number and spacing of the individual clamping fingers as well as the width thereof especially correspond to the number and the spacing of the slits as well as to the width (recesses 5b) of the guide means 5. Furthermore, the clamping fingers are dimensioned such that they can be inserted in the slits without difficulty, which will be discussed in detail hereinafter.

The clamping fingers forming the clamping portion 3d are designed such that they are preferably resiliently flexible in radial direction with respect to the annular portion 3b. For this purpose each clamping finger comprises in the area of its root a predetermined bend which is produced by a thinning of the wall in the radial direction, i.e., the clamping fingers can be resiliently bent at any time within certain limits and automatically return to their original position after bending. The cross-section of each clamping finger is preferably increased almost linearly from its root in the direction of its free end. Thereby each clamping finger has the form of a wedge seen in axial direction. Likewise the clamping fingers extend in axial direction of the annular portion 3b such that they project outwardly increasingly radially in the direction of their free ends. As an alternative embodiment to the wedge-shaped clamping fingers, clamping fingers are imaginable which are dimensioned in such a way that they have no continuous course of cross-section (as the wedge-shaped clamping finger) but consist of a portion of small cross-section and an adjacent portion of large cross-section so that a so-to-speak sudden increase in cross-section takes place. It is preferred, however, that the clamping portion 3d is formed of a plurality of wedge-shaped clamping fingers so as to be able to exploit a wedge effect, which will be discussed in detail hereinafter.

Each wedge-shaped clamping finger comprises at its radially inner side as well as in the area of its free end an engaging surface 3e, as this is illustrated in FIG. 1. The engaging surface 3e in general is such that it has a high roughness, i.e. it produces a high friction coefficient in the engaged state (during contact) with the element to be driven. Preferably a toothing structure is chosen for the engaging surface 3e which is similar to the structure of a toothed rack, for instance. The radially outer surface of each wedge-shaped clamping finger has a very smooth design in contrast to the engaging surface so as to minimize any friction between the latter and another surface or another part, i.e. so as to form a slide surface.

Finally the engaging component 3 comprises a clamping member 3k in addition to the engaging member 3a. In the present case the clamping member 3k has an annular shape, is provided at the outer circumference with a catch, preferably a projection or cam 31 (adapted to be modified in the same way as the projection 3c of the annular portion 3b of the engaging member), which catch may be designed equal or similar to the afore-mentioned projection 3c of the annular portion 3b of the engaging member 3a, and comprises at the inner circumference thereof a plurality of grooves 3n (or recesses) extending in axial direction of the annular clamping member 3k which are spaced evenly along the circumference in accordance with the wedge-shaped clamping fingers of the engaging member 3a. The grooves 3d extend at the inner circumference of the clamping member 3k along the entire length thereof and can be conically beveled preferably with respect to the axial direction of the annular clamping member 3k on the groove bottom thereof so as to further make use of the wedge effect, as will be described below in detail. Furthermore, the dimensions of the clamping member 3k are preferably identical to those of the annular portion 3b of the engaging member 3a, i.e. equal inner and outer diameters (with small oversize) etc.

The engaging member 3a and the clamping member 3k of an engaging component of the engaging means 3 are arranged with respect to each other in accordance with the above-described structure such that the annular portion 3b of the engaging member 3a and the annular clamping member 3k are arranged to be axially adjacent and concentric, the clamping portion 3d in the form of wedge-shaped clamping fingers being inserted in the corresponding grooves 3n of the clamping member 3k. Thus, due to the preferably elastic bending property of the wedge-shaped clamping fingers of the engaging member 3a inserted in the respective grooves 3n of the clamping member 3k, the annular clamping member 3k can be displaced relative to the engaging member 3a in the axial direction thereof, the latter being guided by the wedge-shaped clamping fingers and the grooves 3n.

The clamping member 3k and the engaging member 3a arranged with respect to each other constitute one single engaging component of which the engaging means 3 includes at least two, as mentioned in the foregoing. The at least two engaging components are movably guided by the guide means 5 and by the recesses 5b (longitudinal slits) of the tubular component 2a in the axial direction thereof. That means in detail that the engaging component is arranged in the guide means 5 on the central portion of the tubular component 2a. Just as well also an arrangement is possible in which the corresponding engaging component, depending on the dimensioning thereof, is arranged approximately at the transition between the corresponding end portion and the central portion.

The wedge-shaped clamping fingers of the engaging member 3a are provided in the appropriately formed recesses 5b (longitudinal slits) of the guide means 5, whereby the wedge-shaped clamping fingers of the engaging member 3a are guided according to the course of the longitudinal slits in the axial direction of the tube member. Thus, each engaging component of the engaging means 3 is movably arranged in axial direction of the tubular component 2a. Furthermore, also the engaging member 3a and the clamping member 3k are movably arranged relative to each other, as can be taken from the afore-mentioned structure, because the wedge-shaped clamping fingers of the engaging member 3a are in sliding engagement with the corresponding grooves 3n of the clamping member 3k or, rather, are slidingly inserted in the corresponding guiding grooves 3n of the clamping member 3k.

For driving and controlling the movement of the two engaging components movably disposed at an axial distance from each other on the guide means 5 the discontinuous linear drive 1 according to the preferred embodiment of the invention includes a drive/movement control means 6. This drive means 6 is preferably designed in the form of a hollow cylinder or a collar having at least one internal connecting member. The collar-shaped drive means 6 is arranged concentrically with respect to the tubular component 2a and surrounds the same. Consequently, the tubular component 2a is provided in the cavity of the collar-shaped drive means 6. Furthermore the collar-shaped drive means 6 comprises at the two axial ends thereof a bearing portion 6a which is connected to the corresponding bearing means 4 of the guiding component 2. In this way the collar-shaped drive means 6 is rotatably supported about the axis thereof on the tubular component 2a, but it is immobile in the axial direction thereof with respect to the tubular component.

In the case of the afore-described embodiment according to which the bearing means 4 is designed in the form of the above-mentioned groove 4a at the end portion of the tubular component 2a in which groove the above-mentioned slide ring 4b is inserted, the bearing portion 6a disposed at each axial end of the collar-shaped drive means 6 likewise has the form of a groove extending along the inner circumference of the collar-shaped drive means 6 in which the projecting portion (outer circumferential portion) of the slide ring 4b inserted in the groove 4a is inserted. Consequently, a preferred type of bearing between the collar-shaped drive means 6 and the bearing means 4 is described, but other types of bearing are equally possible as long as the collar-shaped drive means 6 is rotatably mounted on the tubular component 2a.

Moreover, the collar-shaped drive means 6 includes a connecting member or hereinafter also referred to motion control means 6b provided at the inner circumference which is provided, in the preferred embodiment, as a plurality (in the present case four corresponding to the number of engaging and clamping members) of groove or cam curves arranged at the inner circumference. The individual cam curves are provided successively in an axial direction of the collar-shaped drive means 6, each individual one having a closed, so-to-speak annular course. To put it more concretely, each of the cam curves is designed such that it is in sliding engagement with a corresponding catch of one of the engaging or clamping members so as to cause an axial movement of the respective slidingly engaged engaging or clamping member during rotation of the collar. In so far the motion stroke and the motion phase of each of the engaging or clamping members is determined via the individual grooves in the collar. The exact constructional description of the course of each cam curve is renounced in this place and it is referred to the following part of the functional description of the present invention. It is only mentioned that in the present preferred embodiment the collar is formed of two shells which are joined during assembly on the tubular component, each shell including the above-mentioned connecting member guide on its inside. In this way different motion strokes and motion phases can be brought about by exchanging and/or combining individual collar shells.

In the present invention two cam curves juxtaposed in axial direction of the collar-shaped drive means 6 are in sliding engagement at a time with the preferably hemispherical catches of the engaging member 3a and the corresponding clamping member 3k which form an engaging component. In this context it is pointed out that, as in the case of the modifications of the catches 3c and 31 of the engaging member 3a and the clamping member 3k, also in this case respective configurations of the cam curves can be made, as long as the corresponding engagement or sliding engagement can be brought about. So the plurality of cam curves can be formed, for instance, on the outside of the engaging members and clamping members, whereas at the inside of the collar an engaging projection protrudes radially inwardly.

The number of cam curves is dependent, as already indicated, on the number of engaging components. This means in the present invention that when using at least two engaging components at least four cam curves which are engaged with the corresponding hemispherical catches of the engaging components are provided peripherally at the inner circumference of the collar-shaped drive means 6.

For rotating the above-described collar-shaped drive means the same includes in the preferred embodiment a toothing (ring gear 6c) formed at the circumference thereof which is in mesh with a transmission or the like driven, for example, by a motor (not shown). Moreover, a toothing 6c needs not to be provided necessarily. Any other means which is capable of rotating the collar-shaped drive means 6 is suited. For instance, a belt drive or the like can equally be used for this purpose.

Hereinafter the operation of the discontinuous linear drive 1 is described in detail.

In order to operate the discontinuous linear drive the drive means 6 is moved. In the case of the collar-shaped drive means 6 which is rotatably supported about the longitudinal axis thereof by means of the appropriate bearing portions 6a and the bearing means 4 of the tubular component 2a, it is made to rotate by the motor, the transmission or the like, while the tubular component 2a is in a stationary position. By rotation of the collar-shaped drive means 6 about the tubular component the engaging means is driven by the motion control means 6b of the drive means 6. In the event of the motion control means 6b in the form of cam curves, the preferably hemispherical catches 3c and 31 of the respective engaging components which are in engagement or in sliding engagement with the same are guided, i.e. the movement of rotation of the collar-shaped drive means 6 is converted to a translational movement of the respective engaging component (preferably two engaging components) whose direction corresponds to the axial direction of the tubular component. Since at least two engaging components of the engaging means are used in the discontinuous linear drive 1, two cam curves are provided for each engaging component, one of which is in sliding engagement with the hemispherical catch 3c or the engaging member 3a and the other is in sliding engagement with the hemispherical catch 31 of the clamping member 3k.

In order to design the course of the respective cam curves in an as simple way as possible, it is advantageous to arrange the members of an engaging component in such manner that the hemispherical catches 3c, 31 thereof are arranged opposed to each other at the outer circumference of the annular portion 3b and at the outer circumference 3m of the clamping member 3k, i.e., they adopt the same radial position and angular position.

By the guide means 5 in the form of longitudinal slits, which are preferably evenly spaced over the circumference of the tubular component, both engaging components are fixedly held, because the wedge-shaped clamping fingers 3d of the engaging member 3a are inserted in the longitudinal slits. Likewise the clamping member 3k is also fixedly held, because the grooves 3n provided at the inner circumference thereof are engaged with the wedge-shaped clamping fingers of the engaging member 3a. As a consequence, merely a movement of the engaging component in the axial direction of the tubular component 2a is possible, wherein also the engaging member 3a and the clamping member 3k are movable relative to each other in the axial direction of the tubular component 2a by virtue of the afore-mentioned groove-and-finger connection.

Thus, the course of the cam curves is adapted to control both the axial movement of an engaging component as a whole and the movement of the two members of the engaging component, the engaging member 3a and the clamping member 3k, relative to each other.

Accordingly, both members of an engaging component are moved apart from each other as well as toward each other again by the course of the respective cam curves. If both elements are moved apart from each other this entails that the originally radially outwardly bent or projecting wedge-shaped clamping fingers are pressed by means of the grooves 2n of the clamping member 3k the further radially inwardly the further they are moved apart from each other (wedge effect). Consequently, by the relative movement of the two members of an engaging component the wedge effect is exploited the extent of which depends on the design of the wedge-shaped clamping fingers and the above-mentioned possibly beveled surfaces of the grooves 3n. If the course of the cam curves is reversed so that both members are moved toward each other, the wedge-shaped clamping fingers of the engaging member 3a return to the original position thereof, namely projecting further radially outwardly again, due to the elasticity thereof.

In the case of members of an engaging component spaced apart from each other, the wedge-shaped clamping fingers of the engaging member 3a are pressed through the longitudinal slits and an engaging state with the component to be driven, such as an endoscope shaft, is brought about by the fact that the engaging surfaces 3e engage the member to be driven disposed in the tubular component 2a. The engaging state is released again when both members are moved toward each other so that they are adjacent to each other.

Thus, by control of the distance of the two elements of an engaging component the engaging state can be brought about and released. If the distance of the two members of an engaging component is not varied but both members are moved toward each other uniformly and in parallel, the respective state is maintained and either the member to be driven is moved, if the engaging state exists, or the engaging member is moved without moving the member to be driven, i.e. in the case of the released state.

Hence, with a suitable course of the cam curves and a corresponding phase shift of the motion strokes defined hereby, the engaging components can be controlled such that they bring about the engaged state alternately and shifted in phase, respectively, and move along the axial direction of the tubular component 2a while maintaining the engaged state, thereby the member to be driven being moved forward. In detail this means that while the one engaging component is controlled such that it engages in the member to be driven and moves in a longitudinal direction of the tubular component 2a, the other engaging component is in a released state and moves in the opposite direction. As soon as the one engaging component has moved the member to be driven in accordance with the cam curves by a predetermined stroke (dependent on the course of the cam curves) and is in transition to the released state, the other engaging component is in the transition to the engaged state by the course of the cam curves, whereby the member to be driven is moved forward or driven by a predetermined stroke alternately by the two engaging components. Therefore, the course of the cam curves can be described such that they hold an engaging component in the engaged state and move it by a predetermined stroke in a longitudinal direction of the tubular component by virtue of the rotation of the collar-shaped drive means 6. As soon as the one engaging component releases its engaged state and the other one brings about its engaged state, the cam curves extend in such manner that they return the one engaging component provided in the released engaging state to the original position thereof. As a consequence, the cam curves extend such that they do not change their mutual distance, when a state is to be maintained, and change their mutual distance (in the direction of the respective state), when the current state is to be changed.

It is noted that the drive means of the component to be driven depends on the direction of rotation of the collar-shaped drive means 6, i.e. that in the case of reversal of the direction of rotation of the collar-shaped drive means 6 the driving direction of the component to be driven is likewise reversed.

As mentioned already in the foregoing, the number of engaging components is not restricted to two. There may be equally used more than two engaging components, as long as the afore-described pattern is complied with due to the course of the cam curves. So, for instance, in the case of four engaging components, two engaging components can be simultaneously engaged with the element to be driven and move the same forward by a predetermined stroke, while the other two are in a released state. The further course is analogous as described already.

In this way, the element to be driven is driven forward almost continuously by predetermined strokes, wherein the above-described drive is preferably used in everting tube constructions for endoscopes. That is to say that the everting tube including the endoscope shaft of an endoscope is inserted in the tubular component 2a and thus an endoscope drive which continuously encloses the everting tube is provided.

As described in the foregoing, the control of the states of the respective engaging component is performed purely mechanically, i.e. by controlling the distance of the two elements of an engaging component making use of the wedge effect. Thus, electronic control means can be dispensed with. It is another alternative embodiment to control the above-mentioned states in a fluid-operated manner. So the respective engaging member is moved by means of the pertinent cam curve and instead of the mechanical clamping member an appropriate pressure is applied to the respective projections for bringing about the engaged state by controlling a fluid pressure. The principle of the fluid-operated pressure control is analogous to the above-described principle. Therefore a detailed description of the same is dispensed with.

The invention claimed is:

1. A discontinuous linear drive comprising: a guiding component guiding a member to be driven and an engaging means which has two linearly movable engaging components spaced along the guiding component and being adapted to be engaged with the member to be driven and which drives the guided member by a phase-shifted effecting and releasing of the respective engagement of the movable engaging components, wherein for actuating the engaging components, a drive means is provided in the form of a rotatably supported collar surrounding the guiding component, the collar being formed with an internal connecting member or motion control means which is engaged with the engaging components, wherein the connecting member or the motion control means is in the form of a plurality of cam curves peripherally formed at an inner circumference of the collar-shaped drive means and being in sliding engagement with a correspondingly shaped sliding portion.

2. A discontinuous linear drive according to claim 1, wherein each of the at least two engaging components comprises an engaging member and a clamping member whose different positions with respect to each other either bring about or release an engagement.

3. A discontinuous linear drive according to claim 1, wherein each of the at least two engaging components comprises an engaging and a clamping member which establish an engaged state when the engaging member and clamping member are in a moved apart position and release the engaged state when the engaging member and the clamping member are in a moved together position.

4. A discontinuous linear drive according to claim 3, wherein the motion control means or the connecting member moves the at least two engaging components as a whole and varies the position of the engaging and clamping member of an engaging component with respect to each other.

5. A discontinuous linear drive according to claim 1, wherein the engaging member includes an annular portion and a clamping portion, the clamping portion being in the form of a plurality of wedge-shaped and bendable clamping fingers which project in an axial direction with respect to the annular portion and which are bent slightly radially outwardly with respect to the annular portion by virtue of their wedge-shaped design.

6. A discontinuous linear drive according to claim 5, wherein the clamping member has an angular shape at an inner circumference of which a plurality of grooves is provided in which the plurality of wedge-shaped clamping fingers of the engaging member is inserted.

7. A discontinuous linear drive according to claim 6, wherein the tubular component has a guide means in the form of a plurality of recesses arranged at a portion of the tubular component distributed along the circumference thereof, with the plurality of wedge-shaped clamping fingers of the engaging member being inserted in said recesses.

8. A discontinuous linear drive according to claim 1, wherein it is completely constructed of injection molded components.

9. A discontinuous linear drive according to claim 1, wherein the member guided by the guiding component being formed as a tubular component is an everting tube construction comprising an endoscope shaft which is driven by the linear drive.

10. A discontinuous linear drive according to claim 7, wherein the pluralities of recesses are longitudinal slits.

11. A discontinuous linear drive according to claim 1, wherein the sliding portion is a clamping finger of the engaging member.

12. A discontinuous linear drive according to claim 1, wherein the sliding portion is a catch of at least one of the engaging components.

* * * * *

UNITED STATES PATENT AND TRADEMARK OFFICE
CERTIFICATE OF CORRECTION

PATENT NO. : 7,513,359 B2 Page 1 of 1
APPLICATION NO. : 11/432709
DATED : April 7, 2009
INVENTOR(S) : Konstantin Bob and Fritz Pauker It is certified that error appears in the above-identified patent and that said Letters Patent is hereby corrected as shown below:

On the title page item [56]:
In the second column on the cover, under the heading "Foreign Patent Documents", replace "WO 0208035" with -- WO 02068035 --

Signed and Sealed this

Second Day of June, 2009

JOHN DOLL
*Acting Director of the United States Patent and Trademark Office*